United States Patent [19]
Light et al.

[11] Patent Number: 4,565,095
[45] Date of Patent: Jan. 21, 1986

[54] SOUND TRANSDUCER APPARATUS SYSTEM AND METHOD

[75] Inventors: Glenn M. Light; William R. Van der Veer, both of San Antonio, Tex.

[73] Assignee: Southwest Research Institute, San Antonio, Tex.

[21] Appl. No.: 606,276

[22] Filed: May 2, 1984

[51] Int. Cl.⁴ ............................................. G01N 29/00
[52] U.S. Cl. ....................................... 73/621; 73/629; 73/633
[58] Field of Search .................. 73/621, 620, 629, 633

[56] References Cited

U.S. PATENT DOCUMENTS

| | | | |
|---|---|---|---|
| 2,602,102 | 7/1952 | Webb | 73/633 |
| 3,938,372 | 2/1976 | Sproule | 73/633 |
| 4,092,867 | 6/1978 | Matzuk | 73/633 |
| 4,341,120 | 7/1982 | Anderson | 73/621 |
| 4,377,088 | 3/1983 | Evert | 73/633 |
| 4,399,703 | 8/1983 | Matzuk | 73/621 |

*Primary Examiner*—Stephen A. Kreitman
*Attorney, Agent, or Firm*—Hubbard, Thurman, Turner & Tucker

[57] ABSTRACT

An apparatus for emitting and receiving sound signals includes a cylinder into which a sound transducer is mounted. The transducer is mounted to transmit a sound beam normal to the axis of the cylinder. The cylinder is connected to a position detection circuit for determining the angular position of the cylinder about its axis. A system for processing data produced by such a sound transducer apparatus includes circuitry for determining the true position of the cylinder from the position circuit, for alternately causing the transducer to emit and receive sound energy, and for sampling the energy signal received by the transducer when the position detection circuit indicates that the cylinder is at one of several preselected angles. The sampled information is recorded on paper or magnetic media.

19 Claims, 3 Drawing Figures

SOUND TRANSDUCER APPARATUS SYSTEM AND METHOD

BACKGROUND

1. Field of the Invention

The present invention relates generally to sound transducers, and more specially to an apparatus and system for altering the angular position of the transducer and processing the information obtained therefrom.

2. Description of the Prior Art

Ultrasonic detection equipment is routinely used in industry for nondestructive testing of solid materials. For example, steel pipes and plates can be checked for flaws or bad welds by applying pulses of ultrasonic energy to the metal and observing the reflected energy.

Ultrasonic inspection of steel materials is presently an inefficient and time consuming process. An ultrasonic transducer must be moved, by machine or by hand, over the entire surface of the test material being inspected. In order to more accurately determine the subsurface structure of the test material, and to better pinpoint any flaws, this scanning action is repeated with the ultrasonic energy pulses being emitted into the test material at several different angles of incidence. For example, the test material can be scanned with the incident ultrasonic energy impinging thereon at refracted angles of 0°, 45°, and 60°. When three such angles are chosen, three complete scans of the test material must be made. Inasmuch as the testing procedure is identical in all three cases except for the incident angle of the ultrasonic energy, such a process is inefficient.

The prior art shows several methods of changing the incident angle of the ultrasonic energy. One method is to use several different blocks, commonly known as wedges, each of which is shaped so that the transducer transmits the ultrasonic energy at a predetermined angle with the surface of the test material. These blocks are typically made of plexiglass or other material which transmits ultrasonic energy, and are carefully machined to predetermined angles to produce refracted angles, such as the 0°, 45°, and 60° mentioned above. The ultrasonic transducer is attached to this wedge, and passed over the surface of the test material. The transducer is then moved to the next wedge, and the process is repeated. Alternatively, each wedge can have its own transducer, as long as they are carefully matched.

An alternative to the use of individual fixed angle wedges is the use of a single housing which can move a single transducer to various angles. Examples of such devices are shown in U.S. Pat. No. 3,938,372 issued to Sproule, and U.S. Pat. No. 2,602,102, issued to Webb. These variable angle housings allow the use of a single transducer and a single wedge substitute. The incident angle can be set to a first desired value and the scanning process of the test material undertaken. The angle can then be changed, with the scanning process repeated. Although such variable angle housings are an improvement over multiple fixed angle wedges, they still require that the test material be scanned once for each of the preselected test angles.

Since it would be desirable that the complete test be accomplished with a single scan of the test material, it is an object of the present invention to provide an apparatus which is capable of scanning the test material at multiple preselected angles on a single pass. It is a further object of the present invention to provide a system which selects and records the ultrasonic reflection information corresponding only to the preselected angles of incidence.

SUMMARY OF THE INVENTION

In accordance with the present invention, a transducer housing includes a cylinder rotatably mounted therein. A cavity is cut out of the cylinder so that a sound transducer can be inserted therein. An electric motor is coupled of the cylinder through an appropriate linkage arrangement, and causes the cylinder to oscillate through a preselected arc. The transducer is mounted upon the cylinder such that the transducer sound energy beam is transmitted normal to the cylinder axis and at a defined angle with a vertical plane intersecting the cylinder axis. The cylinder axis is connected concentrically to a shaft which, in turn, is connected to a position circuit that determines the angular position of the cylinder shaft. This angular position is the angle of beam transmission by the transducer.

The system includes an interface circuit to decode the beam transmission angle and to transmit the decoded angle to a digital control processor. The sound signals are continuously supplied to the transducer, and are sampled by the control processor only when the transducer is at preselected angles with the surface of the test material. The sampled signals are routed to recorders which record the pertinent sample information for each of the preselected test angles. A single pass over the test material provides testing information for several beam angles.

BRIEF DESCRIPTION OF THE DRAWINGS

The novel features which characterize the present invention are defined by the appended claims. The foregoing and other objects and advantages of the present invention will hereinafter appear, and for purposes of illustration, but not of limitation, an exemplary embodiment is shown in the drawings.

DESCRIPTION OF THE PREFERRED EMBODIMENT

Figure 1:
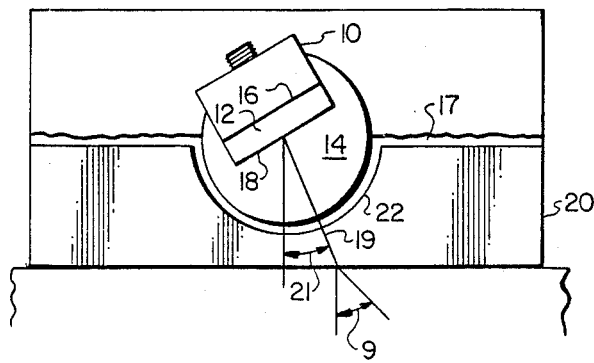
FIG. 1 is a side view of a preferred transducer housing according to the present invention.

FIG. 1 is a simplified, cutaway side view of a variable angle ultrasonic transducer housing constructed according to the present invention. A standard ultrasonic transducer 10 is mounted in an appropriately shaped cavity 12 of a plastic cylindrical mount 14. The emitting surface 16 of the ultrasonic transducer 10 is planar, and the matching surface 18 of the cylinder cavity 12 passes through the axis of the cylinder 14. For illustration, the transducer emitting surface 16 is offset from the matching surface 18 to illustrate the cylinder cavity 12. In operation, the emitting surface 16 is adjacent to the matching surface 18. A lower block 20 has a matching hemicylindrical cutout 22. The cylinder 14 is rotatably mounted so that the cylinder 14 axis and the axis of the hemicylindrical cutout 22 approximately coincide. The space between the cylinder 14 and the block 20 is filled with a coventional couplant grease 17. In the preferred embodiment, such couplant grease would include water, oil or vacuum grease.

As shown in FIG. 1, the spacing between the cylinder 14 and the block 20 is greatly exaggerated. In ultrasonic inspection of metal pipes and similar materials, frequencies in the range of approximately 1 to 10 MHz are typical. It is preferable that the spacing between the cylinder 14 and the block 20 be a known function of the wavelength of ultrasound in the couplant medium. In the preferred embodiment, the spacing is equal to one quarter the wavelength of the ultrasonic energy to be used.

The lower face 18 of the cylinder cavity 14 passes through the axis of the cylinder 14. This causes energy to be emitted from the transducer 10 at a consistent height above the surface of test material which is in contact with the lower surface of the block 20 and, further, normal to the cylinder axis. The ultrasonic beam 19 is thus transmitted at an angle 21 identical to the angular position of the cylinder axis relative to a vertical plane normal to the surface of block 20. The shaft of the cylinder is connected to position circuitry (not shown) to detect the angular position of the cylinder shaft. This angular position is identical to the ultrasonic transducer beam angle. In the preferred embodiment, the cylinder shaft is connected to a potentiometer that provides a voltage output indicative of the beam angle.

Figure 2:
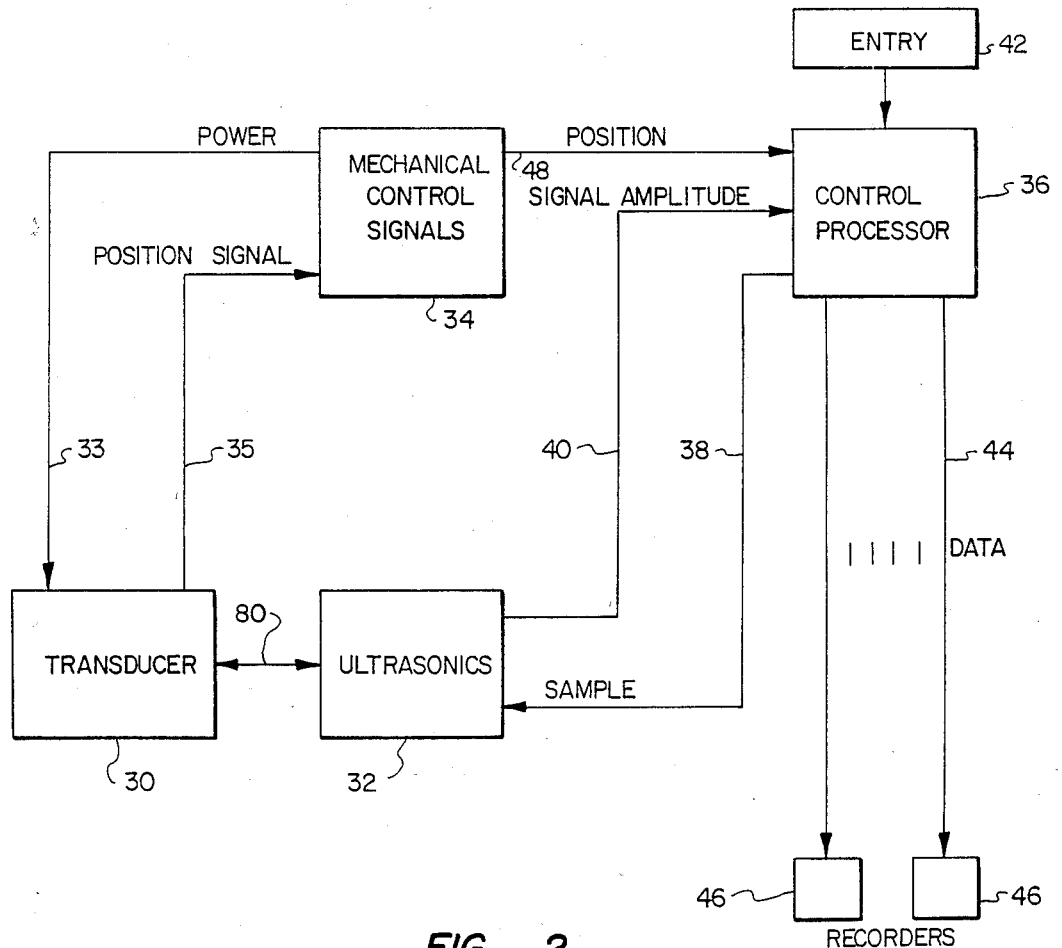
FIG. 2 is a block diagram illustrating the control system of the preferred embodiment.

Referring to FIG. 2, a complete system utilizing the concept of the present invention is depicted. An ultrasonic transducer package 30 embodies the variable angle concept shown in FIG. 1. An ultrasonics control unit 32 is coupled to the transducer portion 10 of the variable angle unit 30 via line 80, and causes the transducer 10 to emit ultrasonic energy and detect reflected energy. This is done in a conventional manner, as, for example, by alternately applying power to the transducer 10 and "listening" for echoes at a 1 KHz or other high rate. A mechanical control signal buffer 34 applies power to the potentiometer 60 on line 35 and detects an electrical voltage on position signal line 35 which is proportional to the angular position of the cylinder 14. The circuitry for providing this position signal will be described in connection with FIG. 3. A control processor 36, which is preferably a conventional microprocessor, is coupled to the mechanical control signal buffer 34 and the ultrasonic circuitry 32. The position signal is digitized in the control signal buffer 34 and coupled to an input of the control processor 36. A sample output line 38 from the control processor 36 is coupled to the ultrasonic circuitry 32 and acts as a gating control. That is, receipt of a signal on the sample line 38 causes the reflected energy level received by the transducer 10 to be coupled to the control processor 36 as a signal amplitude on line 40. The signal amplitude data transferred on line 40 to the control processor 36 can be in either analog or digital form, depending upon the particular application and configuration of the system.

A control and data entry interface 42 for use by the operator is coupled to the control processor 36. Output data lines 44 are coupled to the control processor 36 and to recorders 46 as needed. These recorders 46 can be, for example, strip chart paper recorders or magnetic tape or disc units for storing digitized output.

Operation of the system of FIG. 2 will now be described. Electrical power is applied to the transducer device 10 on the power line 80, causing the transducer to emit an ultrasonic beam 19. A motor is powered which is coupled to the cylinder and causes the cylinder 14 to rotate thus varying the angle at which the ultrasonic energy emitted by the transducer 10 will encounter the surface of a test material as described in connection with FIG. 1. The ultrasonics circuitry 32 alternately applies power to the transducer 10 and listens to any reflections. The cylinder 14 oscillates at a variable frequency from zero to less than 30 Hz, and a voltage which is proportional to the angle between the emitted energy beam and a vertical plane normal to the surface of the test material is transmitted to the mechanical control signal interface 34 on line 35. In the example presently described, the position signal is digitized by the interface 34, with the digitized position signal coupled to the control processor 36 on line 48.

Through the control and data entry interface 42, the angles of interest can be entered into the control processor 36. For example, incidence angles of 0°, 37°, and 48° are common. From the selected incidence angle, a refractive angle 9 may be determined by applying Snell's Law. When the digitized position signal indicates that the transducer 10 is transmitting and receiving at one of these preselected angles, a sample request signal is generated by the control processor 36 and applied to line 38. The corresponding reflected energy level is detected by the control processor 36 on line 40. In the preferred embodiment, the ultrasonic signal amplitude is detected in analog form, and coupled to the proper recorder output line 44 by analog switches contained within the control processor 36. The recorders 46 can be strip chart recorders, and each recorder 46 corresponds to one of the refractive angles 0°, 45°, or 60°. The analog input from the ultrasonic circuitry 32 is thus routed to the correct corresponding recorder 46. When recorders 46 with a slow response time are used, the sampling rate of 16 to 20 Hz for each preselected angle, which is twice the oscillation rate of the cylinder 14 causes a fairly smooth record to be generated by the recorders 46.

In an alternative embodiment, the level information from the ultrasonic circuitry 32 is digitized, with the sampled values recorded on magnetic discs or tape for later computer analysis.

Figure 3:
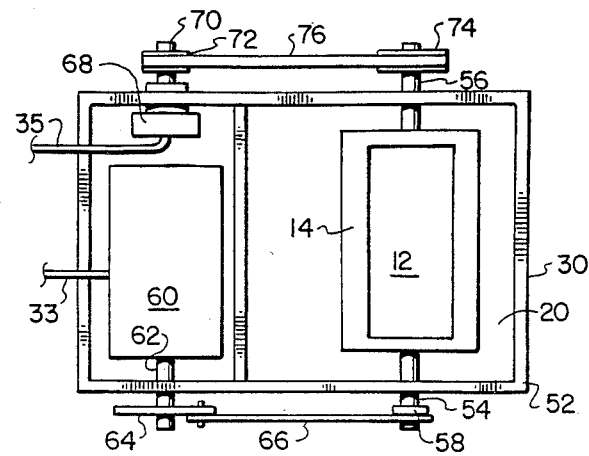
FIG. 3 is a top view of a preferred transducer housing according to the present invention.

Referring to FIG. 3, a preferred embodiment of a transducer housing unit 30 for the ultrasonic transducer 10 is shown. In this view, the transducer 10 has been removed from the cylinder 14.

A single casing 52 houses the various parts of the transducer housing unit 30. A power shaft 54 is coupled to the cylinder 14 along its axis and projects through one wall of the casing 52. A position shaft 56 is coupled to the cylinder 14 at the opposite end, and also projects through the casing 52. The cylinder 14 is thus rotatably mounted above the lower block 20 with the cylinder cavity 12 upright. A conventional grease couplant 17 resides between the cylinder 14 and the block 20 as described with respect to FIG. 1. An arm 58 is connected to the power shaft 54, and as shown in FIG. 3, projects upward from the plane of the drawing. A DC motor 60 is coupled to the casing 52 so that its shaft 62 projects through the wall of the casing 52. A disc 64 is attached to the end of the motor shaft 62, and a linkage arm 66 is rotatably coupled to the disc 64 and the arm 58. The sizes of the disc 64, linkage arm 66, and arm 58 are chosen in a conventional manner so that the cylinder 14 will oscillate through a predetermined arc while the disc 64 rotates in a complete circle. In the preferred embodiment, the cylinder 14 oscillates so that the angle of the ultrasonic energy beam emitted from the transducer produces refracted angles that vary from 0 to 70 degrees with respect to the normal to the surface of a test material upon which the transducer housing unit 30 is placed.

A conventional variable resistor 68 is coupled to the casing 52 with its shaft 70 projecting therethrough as shown. A resistor sprocket 72 and a cylinder sprocket 74 are coupled to the resistor shaft 70 and the cylinder position shaft 56 respectively. A conventional plastic timing belt 76 is tightly looped around both sprockets 72, 74, whereby the variable resistor 68 is slaved to the motion of the cylinder 14 axis. The teeth ratio of these sprockets 72, 74 is chosen in a conventional manner, and is preferably chosen so that the variable resistor 68 turns through most of the available angle for rotation while the cylinder 14 turns through its limits of oscillation. A voltage is applied through the resistor 68 to position wires 35, and a large variance in the resistance results in an easily discriminated voltage signal across the position wires 35.

When power is applied to the motor 60 through the power wires 33, the motor 60 operates and causes the cylinder 14 to oscillate as described above. As the cylinder 14 oscillates, the resistance of the slaved variable resistor 68 changes, so that the voltage drop across the resistor 68 changes in proportion to the angular position of the cylinder 14. An A-D converter in the mechanical control signals interface 34 can be calibrated in a conventional manner so that the digital position data indicates the angular position of the cylinder 14 directly. Generally, the speed of the motor 60 is not critical, nor is the arc through which the cylinder 14 oscillates as long as the preselected angles are included. Since the reflected signal is sampled only when the cylinder 14 is at the predetermined angles, extra movement of the cylinder 14 does not affect the information routed to the recorders 46 by the control processor 36.

Although a preferred embodiment has been described in detail, it should be understood that various substitutions, alterations and changes may become apparent to those skilled in the art. These modifications may be made without departing from the scope and spirit of the invention as defined by the appended claims.

What is claimed is:

1. A sound transducer apparatus comprising:
 sounding means for generation of directional sound energy and for receiving sound energy;
 a rotational movable mount means connected to said sounding means for varying the angular direction of sound energy while maintaining a costant distance above a test material surface; and
 position detection means for determining the direction of generated sound energy.

2. A sound transducer according to claim 1 wherein said sounding means includes a controllable sound transducer.

3. A sound transducer according to claim 2 wherein said mount means includes a cylinder housing connected to said sound transducer, said cylinder housing connected to a cylindrically receiving mount such that the cylinder housing is rotationally movable about an axis with said cylindrical receiving housing while maintaining a center portion of the sound transducer at a constant distance above the test material surface.

4. A sound transducer apparatus according to claim 3 wherein said sound transducer is mounted upon said cylinder housing such that the direction of sound energy is normal to and angularly rotatable about said axis.

5. A sound transducer according to claim 4 wherein said mount means includes a motor means for rotating said cylinder housing about said axis and located at an offset distance from the cylindrical housing.

6. A sound transducer apparatus according to claim 5 wherein said position detection means is connected to said cylinder housing for detecting the angular position of said cylinder housing about said axis.

7. A sound transducer apparatus according to claim 6 wherein said position detection means includes output circuitry for outputting said detected angular position.

8. A sound transducer apparatus according to claim 7 wherein said motor means rotates said cylinder housing in an oscillatory manner.

9. A sound transducer apparatus according to claim 8 including control means for controlling the frequency of sound generation by said sound means.

10. A sound transducer apparatus system comprising:
 a sound transducer means for generating a directional sound energy beam and for detecting reflected sound waves;
 a mounting means connected to said sound transducer means for angularly rotating the direction of said sound energy beam at a constant distance from a surface of test material;
 angular position detection means for determining the angular position of said sound energy beam; and
 control means connected to said sound transducer means for controlling said sound generation and sound reception by said transducer, and connected to said mounting means for controlling the direction of said sound energy beam.

11. A sound transducer apparatus system according to claim 10 further including recording means for recording data including sound received by said transducer and position angle of the transducer when the sound was received.

12. A sound transducer apparatus system according to claim 11 wherein said mounting means includes a cylinder housing connected to said sound transducer means, said cylinder housing connected to a cylindrically receiving mount such that the cylinder housing is rotationally movable about an axis with said cylindrical receiving mount, said sound transducer means connected to the cylinder housing at the axis such that the center of the sound transducer maintains a constant distance above a test material surface in contact with a cylindrical receiving mount surface opposite the cylindrical receiving mount surface connected to the cylindrical housing.

13. A sound transducer apparatus system according to claim 12 wherein said sound transducer means is mounted upon said cylinder housing such that the direction of sound energy is normal to and angularly rotatable about said axis.

14. A sound transducer apparatus system according to claim 13 wherein said mounting means includes a motor means located at an offset distance from and mechanically connected to the cylinder housing for rotating said cylinder housing about said axis.

15. A sound transducer apparatus system according to claim 14 wherein said position detection means is connected to said cylinder housing for detecting the angular position of said cylinder housing about said axis.

16. A sound transducer apparatus according to claim 15 wherein said position detection means includes a variable resistor axially connected to said cylinder housing for providing a voltage proportional to the angular position of said axis.

17. A sound transducer apparatus according to claim 16 wherein said oscillatory rotation of said cylinder housing varies from 0 hertz to less than 30 hertz.

18. A sound transducer according to claim 17 wherein said cylinder housing is separated from said cylindrical receiving mount by a couplant medium and the distance between the cylinder housing and said cylindrical receiving mount is specific portion of a wavelength of a frequency from the transducer.

19. A method for obtaining a plurality of reflective sound signals suitable for determining internal structure characteristics of test material comprising the steps of:
 (a) alternately energizing and deenergizing a directional sound transducer, wherein directional pulses of sound are generated;
 (b) measuring, between the generated pulses, ultrasonic energy reflected back to the transducer;
 (c) varying the angle between the directional energy pulses and a surface of the test material while maintaining a center portion of the sound transducer above the test material surface at a constant distance;
 (d) generating an electrical position signal which is proportional to the angle between the directional energy pulses and normal to the surface of the test material;
 (e) calculating the angle between the directional energy pulses and the normal to the surface of the test material from the value of the position signal;
 (f) comparing the calculated angle to at least one preselected value; and
 (g) sampling the reflected energy when the calculated angle is the same as at least one preselected value.

* * * * *

UNITED STATES PATENT AND TRADEMARK OFFICE
CERTIFICATE OF CORRECTION

PATENT NO. : 4,565,095
DATED : January 21, 1986
INVENTOR(S) : Glenn M. Light and William R. Van der Veer It is certified that error appears in the above-identified patent and that said Letters Patent is hereby corrected as shown below:

Column 1, line 8, "specially" should be --specifically--.

Column 2, line 66, "covential" should be --conventional--.

Column 5, line 49, "costant" should be --constant--.

Signed and Sealed this

Fifteenth Day of April 1986

[SEAL]

Attest:

DONALD J. QUIGG

Attesting Officer  Commissioner of Patents and Trademarks